United States Patent [19]

Vargas Garcia

[11] Patent Number: 4,616,633
[45] Date of Patent: Oct. 14, 1986

[54] RETRACTOR FOR USE IN ORAL AND MAXILLOFACIAL SURGERY

[75] Inventor: Arturo Vargas Garcia, Rio Piedras, P.R.

[73] Assignee: Commonwealth of Puerto Rico, P.R.

[21] Appl. No.: 709,129

[22] Filed: Mar. 7, 1985

[51] Int. Cl.⁴ ............................................. A61B 17/02
[52] U.S. Cl. ...................................................... 128/20
[58] Field of Search ..................... 128/20, 303 R, 304, 128/305

[56] References Cited

U.S. PATENT DOCUMENTS 3,701,348  10/1972  Navara ................................. 128/20
3,853,120  12/1974  Batista ................................. 128/20

FOREIGN PATENT DOCUMENTS 2272632  12/1975  France ................................. 128/20
20446  of 1907  United Kingdom ................. 128/20

Primary Examiner—Jay N. Eskovitz
Attorney, Agent, or Firm—Scrivener Clarke Scrivener & Johnson

[57] ABSTRACT

An instrument for retracting soft tissue during oral and maxillofacial surgery has a handle, a palm engaging lesser blade at one end of the handle and a greater active blade which extends at an adjustable angle from the other end of the handle.

1 Claim, 4 Drawing Figures

RETRACTOR FOR USE IN ORAL AND MAXILLOFACIAL SURGERY

SUMMARY OF THE INVENTION

An instrument for retracting soft tissue during oral and maxillofacial surgery has a central flat handle part with a shorter blade at its one end to be engaged by the surgeon's palm and a longer active blade at its other end having an inturned outer end for engaging and retracting soft tissue, the active blade being connected to the handle by a narrow neck formed of malleable material permitting angular adjustment of the active blade.

DESCRIPTION OF THE INVENTION

The invention provides an instrument to be held in the surgeon's hand during oral and maxillofacial periodontic and endodontic surgical procedures for retraction of soft tissue, including the tongue.

The retractor instrument is formed of a strip of 1/16 inch stainless steel with high corrosion resistance, preferably approximately ½ inch in width. The instrument has a central, straight section 2 forming a handle for manual grasping and manipulation, a lesser active blade 4 at one end of the handle, and a greater active blade 6 at the other end of the handle.

Figure 4:
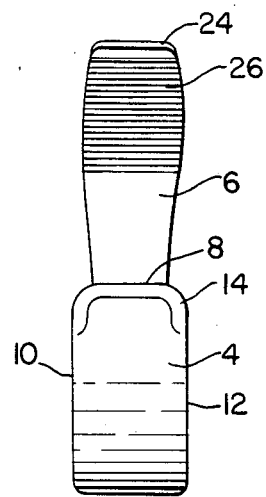
FIG. 4 is an end view of the instrument, taken in the direction of arrow B of FIG. 1.

The lesser active blade 4 is arcuate in shape, being curved from the flat handle part 2 back toward the handle part through an arc of approximately 95° and terminates in an end surface 8 which is normal to the linear sides 10, 12 of the lesser active blade and which is formed with a reduced thickness edge part 14, as particularly shown in FIG. 4, and which in the preferred form of the invention is approximately 1.50 inches above the level of the outer surface of the handle part.

Figure 1:
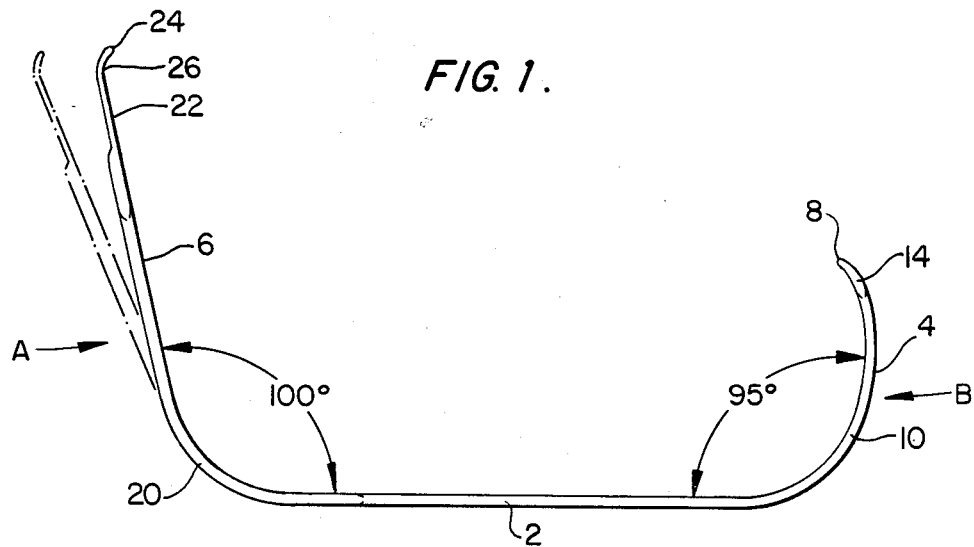
FIG. 1 is a side view of the instrument.
Figure 2:
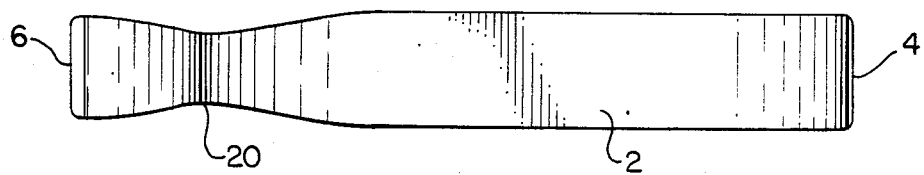
FIG. 2 is a bottom plan view.
Figure 3:
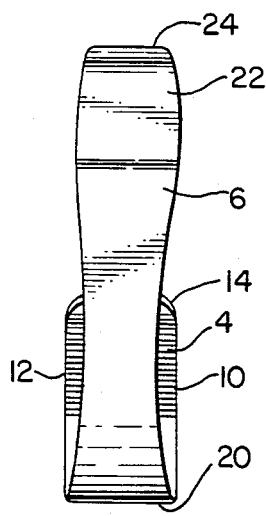
FIG. 3 is an end view of the instrument, taken in the direction of arrow A of FIG. 1.

The greater active blade 6 extends from the end of the handle part opposite to the end formed by the lesser active blade, and is of greater length than the lesser active blade, and I have found that good results are provided if this blade is approximately 2.280 inches in length. In its preferred position, which is shown in full lines in FIG. 1, it is connected to the handle part through a curved section 20 of reduced section and extends from the handle part 2 at an obtuse angle of approximately 100°. At its outer extremity this part of the instrument is reduced in thickness for a length of approximately one inch, as shown at 22, and is provided with a tip end part 24 which is curved inwardly toward the handle and the inner surface of which is roughened as shown in 26. The connecting part of reduced section 22 is formed of malleable material which permits angular adjustment of the greater active blade with respect to the handle, as shown in the dotted line positions of FIG. 1.

In the use of the instrument the handle part 2 is grasped manually by the surgeon's fingers with the surgeon's palm outside and resting on the outer surface 30 of the lesser active blade, thus leaving the greater active blade free for insertion into the oral cavity and manipulation within it, the curved top 24 at the outer end of the blade being particularly useful for preventing slipping of the soft tissue which is being held and retracted by the greater blade.

The configuration of the instrument provides many non-obvious advantages to the surgeon performing operative procedures with which the instrument is useful, among which the following are of great importance: The curvatures of the greater and lesser blades permit rapid and atraumatic access to all parts of the oral cavity. The angle of the greater blade may be increased or decreased to accomodate the instrument to the procedure being performed and to the comfort of the surgeon. Further, the lesser blade may be used as a retractor in the labial vestibule and when used in its normal manner reduces finger fatigue by permitting the palm of the hand to be used to retain the proper position of the instrument in the hand.

I claim:

1. A retractor for soft tissue for use during oral and maxillofacial surgery formed from a strip of flat bendable material of substantially constant width and thickness, and comprising:
  (a) a substantially straight handle part,
  (b) a greater active blade part connected to one end of the handle part through an area of reduced thickness and extending from the handle at an obtuse angle of approximately 100° and having:
    (i) an outer end part of reduced thickness having a tip end curved toward the handle and a patterened inner surface, and
  (c) a lesser active blade part connected to the other end of the handle part the outer end of which is of lesser height above the handle than the outer end of the greater active blade part and being curved throughout its length back toward the handle part through approximately 95°, the connection of the greater active blade part to the handle part being malleable to permit angular adjustment of the greater active blade part with respect to the handle part.

* * * * *